(12) United States Patent
Watanabe et al.

(10) Patent No.: US 10,765,439 B2
(45) Date of Patent: Sep. 8, 2020

(54) TREATMENT METHOD AND MEDICAL DEVICE

(71) Applicant: Terumo Kabushiki Kaisha, Shibuya-ku, Tokyo (JP)

(72) Inventors: Kouhei Watanabe, Fujinomiya (JP); Takayuki Mouri, Fujinomiya (JP); Risa Hoshino, Hadano (JP); Akihiko Tarunaga, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 190 days.

(21) Appl. No.: 15/425,091

(22) Filed: Feb. 6, 2017

(65) Prior Publication Data

US 2017/0224363 A1 Aug. 10, 2017

(30) Foreign Application Priority Data

Feb. 8, 2016 (JP) .................... 2016-022258

(51) Int. Cl.
*A61B 17/22* (2006.01)
*A61M 1/00* (2006.01)
(Continued)

(52) U.S. Cl.
CPC ............ *A61B 17/22* (2013.01); *A61B 17/221* (2013.01); *A61B 17/320725* (2013.01);
(Continued)

(58) Field of Classification Search
CPC ............ A61B 17/22; A61B 17/320725; A61B 2017/00809; A61B 2017/22079; A61B 2017/320012; A61B 2217/005; A61M 25/0082; A61M 2025/0096; A61M 2025/0681; A61M 2025/109; A61M 2025/1093; A61M 29/02; A61M 2210/1035

See application file for complete search history.

(56) References Cited

U.S. PATENT DOCUMENTS 6,652,579 B1 * 11/2003 Cox ................. A61F 2/91
623/1.15
2001/0056219 A1 * 12/2001 Brauckman .......... A61N 5/1002
600/3
(Continued)

FOREIGN PATENT DOCUMENTS

JP 2011/056251 3/2011

*Primary Examiner* — Manuel A Mendez
*Assistant Examiner* — Justin L Zamory
(74) *Attorney, Agent, or Firm* — Thaine Lennox-Gentle; Sheridan Ross, PC

(57) ABSTRACT

Provided is a treatment method of being able to improve the obstruction of a biological lumen caused by stenosis of the biological lumen and the stagnation of a secretion. The treatment method includes a disposition step of disposing a dilation portion that can be dilated and deflated, and a collection portion, which is capable of removing a secretion S secreted from a biological lumen from a living body, in a stenosed site occurring in the biological lumen; a dilation step of widening the stenosed site after the disposition step by dilating the dilation portion in the stenosed site after the disposition step; and a removal step of removing the secretion from the living body by a removal portion.

8 Claims, 9 Drawing Sheets

(51) Int. Cl.

| | | |
|---|---|---|
| | *A61B 17/221* | (2006.01) |
| | *A61M 29/02* | (2006.01) |
| | *A61B 17/3207* | (2006.01) |
| | *A61M 25/00* | (2006.01) |
| | *A61M 25/10* | (2013.01) |
| | A61B 17/32 | (2006.01) |
| | A61B 17/00 | (2006.01) |
| | A61M 25/06 | (2006.01) |

(52) U.S. Cl.
CPC ...... *A61M 1/0001* (2013.01); *A61M 25/0082* (2013.01); *A61M 25/10* (2013.01); *A61M 29/02* (2013.01); *A61B 2017/00809* (2013.01); *A61B 2017/22051* (2013.01); *A61B 2017/22079* (2013.01); *A61B 2017/320012* (2013.01); *A61B 2217/005* (2013.01); *A61M 2025/0096* (2013.01); *A61M 2025/0681* (2013.01); *A61M 2025/109* (2013.01); *A61M 2025/1093* (2013.01); *A61M 2210/1035* (2013.01)

(56) References Cited

U.S. PATENT DOCUMENTS

| | | | |
|---|---|---|---|
| 2007/0213753 A1* | 9/2007 | Waller | A61B 17/3207 606/159 |
| 2011/0056500 A1 | 3/2011 | Shin et al. | |
| 2012/0021037 A1* | 1/2012 | Ladet | A61L 17/145 424/422 |
| 2015/0313732 A1* | 11/2015 | Fulton, III | A61F 2/013 623/1.11 |

* cited by examiner

TREATMENT METHOD AND MEDICAL DEVICE

CROSS REFERENCE TO RELATED APPLICATIONS

The present application claims the benefit of priority, under 35 U.S.C. § 119(e), to Japanese Application No. 2016-022258, filed Feb. 8, 2016, entitled "Treatment Method and Device," the entire disclosure of which is incorporated herein by reference in its entirety, for all that it teaches and for all purposes.

TECHNICAL FIELD

The present invention relates to a treatment method of widening a stenosed site occurring in a biological lumen, and removing a secretion stagnating in the stenosed site and to a medical device that widens a stenosed site occurring in a biological lumen and removes a secretion stagnating in the stenosed site.

BACKGROUND

If a patient is afflicted with chronic bronchitis caused by breathing in harmful substances such as cigarette smoke over a long period of time, a medial wall of a bronchus may thicken due to inflammation, and the bronchus may become narrow. The amount of a secretion such as phlegm may increase due to chronic inflammation of the bronchus, and the secretion may stagnate in a stenosed site. If a substantial lumen of the bronchus, through which air is capable of flowing becomes narrow due to stenosis of the bronchus and the stagnation of a secretion, the flow of air is limited, and thus, normal breathing is disrupted.

A treatment method in which a stenosed site is widened using a medical device including a dilation portion, such as a balloon catheter, which can be dilated and deflated is known as a therapy method that is used in a case where a stenosed site is formed in a biological lumen such as a bronchus (refer to Japanese Patent Application No. JP-2011-56251).

SUMMARY

Problem That is Solved

In contrast, if not only stenosis of a biological lumen but also the stagnation of a secretion may occur as in chronic bronchitis, it is not possible to eliminate the stagnation of the secretion only by widening a stenosed site as described above, and thus, it is not possible to satisfactorily eliminate the obstruction of the biological lumen.

An object of the embodiments herein is to provide a treatment method and a medical device which are capable of improving the obstruction a biological lumen caused by stenosis of the biological lumen and the stagnation of a secretion.

Solving the Problem

According to an aspect of the embodiments herein, there is provided a treatment method including a disposition step of disposing a dilation portion that can be dilated and deflated, and a removal portion, which is capable of removing a secretion secreted from a biological lumen from a living body, in a stenosed site occurring in the biological lumen; a dilation step of widening the stenosed site by dilating the dilation portion in the stenosed site after the disposition step; and a removal step of removing the secretion from the living body by the removal portion after the disposition step.

According to another aspect of the embodiments herein, there is provided a medical device including a long shaft having flexibility; a dilation portion that is disposed in a distal portion of the shaft and can be dilated and deflated; and a removal portion that is capable of removing a secretion secreted from a biological lumen from a living body.

Advantage of the Invention

According to the treatment method of the embodiments herein, it is possible to widen a stenosed site occurring in a biological lumen, and to remove a secretion stagnating in the stenosed site. Accordingly, it is possible to suitably improve the obstruction of the biological lumen caused by stenosis of the biological lumen and the stagnation of the secretion.

The medical device, of the embodiments herein, is capable of widening a stenosed site occurring in a biological lumen, and removing a secretion stagnating in the stenosed site. Accordingly, it is possible to suitably improve the obstruction of the biological lumen caused by stenosis of the biological lumen and the stagnation of the secretion.

DETAILED DESCRIPTION

Figure 1:
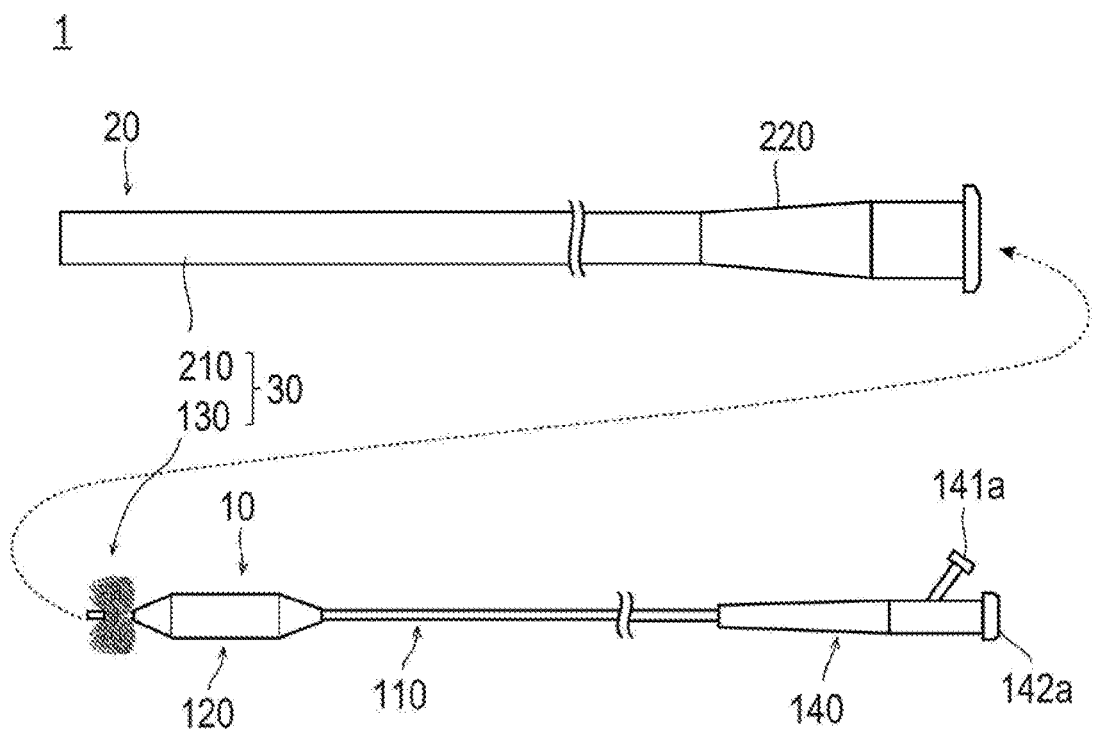
FIG. 1 is a schematic view illustrating the entire configuration of a medical device of a first embodiment.

Hereinafter, embodiments of the will be described with reference to the accompanying drawings. The following description does not limit a technical scope or the meaning of terms described in the claims. For illustrative purposes, the size or ratio of each member in the drawings may be exaggerated and may be different from an actual ratio.

An embodiment of a treatment method and a medical device 1 will be described with reference to FIGS. 1 to 6. FIGS. 1 and 2 are views provided to describe the configuration of each part of the medical device 1. FIGS. 3 to 6 are views provided to describe the treatment method.

The medical device 1 is a medical device used to ensure a substantial lumen of a bronchus through which air is capable of flowing by widening a stenosed site N (refer to FIG. 4) occurring in the bronchus due to chronic bronchitis, and removing a secretion S such as phlegm, which has viscosity and stagnates in the stenosed site N, from a living body (refer to FIG. 6).

In a brief description of the medical device 1 with reference to FIG. 1, the medical device 1 includes a balloon catheter 10 used to widen the stenosed site N and to collect the secretion S, and a protective catheter 20 including a sheath (equivalent to a "protective portion") 210 that is capable of protecting a distal side of the balloon catheter 10 by covering the distal side, and accommodating and then discharging the secretion S, which is collected by the balloon catheter 10, from a living body. Hereinafter, the configuration of each part of the medical device 1 will be described in detail.

First, the balloon catheter 10 will be described. The balloon catheter 10 includes a long shaft 110 having flexibility; a dilation portion 120 that is provided on a distal side of the shaft 110, and can be dilated and deflated by the inflow and discharge of a fluid; a collection portion 130 that is provided on a distal side of the dilation portion 120, and is capable of collecting the secretion S; and a first hand operation portion 140 that is firmly fixed to a proximal portion of the shaft 110. In embodiments, a removal portion 30 which removes the secretion S from the living body includes the collection portion 130 of the balloon catheter 10 and the sheath 210 of the protective catheter 20 which is capable of accommodating and then discharging the collected secretion S from the living body.

Figure 2A:
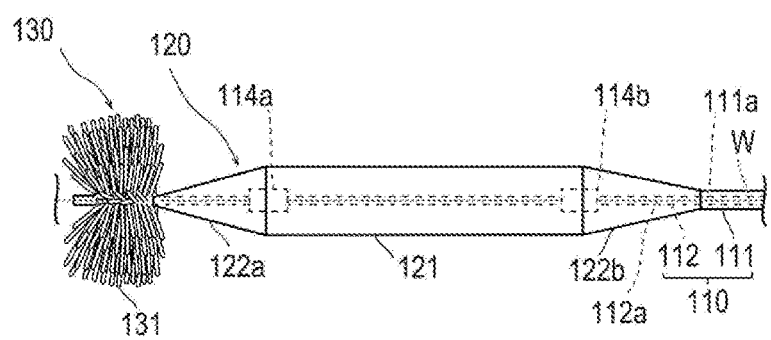
FIG. 2A is an enlarged top view illustrating a distal portion of the medical device of the first embodiment.
Figure 2B:
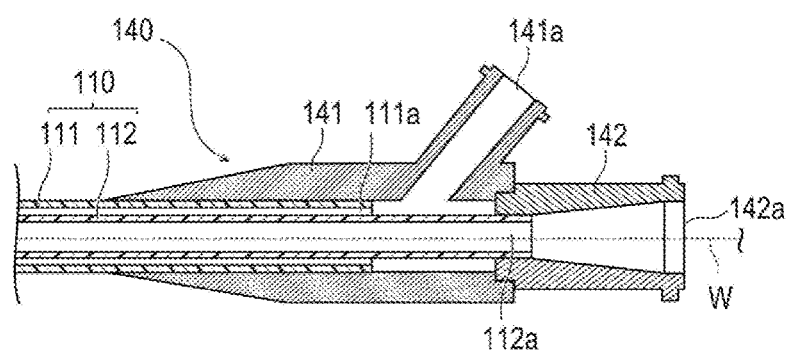
FIG. 2B is an enlarged sectional view illustrating a proximal portion of the medical device of the first embodiment.

As illustrated in FIGS. 2A and 2B, the shaft 110 includes an outer tube 111, which is a tube shaped body with an open distal end and an open proximal end, and an inner tube 112, which is a tube shaped body with an open distal end and an open proximal end, and is disposed in a lumen of the outer tube 111.

In embodiments, an extending direction of the shaft 110 is referred to as an axial direction, a side of the shaft 110 in the axial direction which is inserted into a biological lumen is referred to as a distal side, and a hand-side of the shaft 110 in the axial direction in which the first hand operation portion 140 is provided is referred to as a proximal side. A distal portion indicates a predetermined range including a distal end (distalmost end) and the vicinity of the distal end. A proximal portion indicates a predetermined range including a proximal end (proximalmost end) and the vicinity of the proximal end.

A dilation lumen 111a is formed between an outer peripheral surface of the inner tube 112 and an inner peripheral surface of the outer tube 111, and a dilation fluid for dilating the dilation portion 120 flows through the dilation lumen 111a. As illustrated in FIG. 2B, the dilation lumen 111a communicates to an injection port 141a of the first hand operation portion 140 (to be described later). The fluid may be a gas or a liquid. Examples of the fluid include gases such as helium gas, air, $CO_2$ gas, and $O_2$ gas, and liquids such as physiological salt solution and a contrast agent.

As illustrated in FIG. 2A, the inner tube 112 includes a guide wire lumen 112a through which a guide wire W is inserted. As illustrated in FIG. 2B, the guide wire lumen 112a communicates to a proximal opening portion 142a of the first hand operation portion 140 (to be described later).

As such, the balloon catheter 10 is a so-called over-the-wire type catheter in which the guide wire W is inserted through the proximal opening portion 142a of the first hand operation portion 140 and a distal opening portion of the inner tube 112. The balloon catheter 10 may be a so-called rapid exchange type catheter in which an opening portion communicating to the inner tube 112 is provided somewhere between the distal side and the proximal side of the shaft 110, and the guide wire W is inserted through the opening portion and the distal opening portion of the inner tube 112.

As illustrated in FIG. 2A, a distal portion of the inner tube 112 passes through the inside of the dilation portion 120, and is open while being positioned closer to the distal side than the dilation portion 120 and the collection portion 130. Contrast markers 114a and 114b are installed in the inner tube 112 such that the contrast markers 114a and 114b are respectively positioned at the boundary between a cylindrical portion 121 and a distal tapered portion 122a of the dilation portion 120 and at the boundary between the cylindrical portion 121 and a proximal tapered portion 122b of the dilation portion 120.

The outer tube 111 and the inner tube 112 are formed of a material having flexibility to some extent. The material is not limited to a specific material. The following materials may be used as the material: polyethylene, polypropylene, polybutene, an ethylene-propylene copolymer, an ethylene-vinyl acetate copolymer, an ionomer, polyolefin which is a mixture of two or more thereof, a polyvinylchloride resin, polyamide, a polyamide elastomer, polyester, a polyester elastomer, polyurethane, fluororesin, and the like.

The dilation portion 120 has the function of widening a stenosed site.

The dilation portion 120 is folded on an outer periphery of the inner tube 112 in a state where the dilation portion 120 is deflated. As illustrated in FIG. 2A, the dilation portion 120 includes the cylindrical portion 121 having a substantially constant outer diameter in an extending direction (rightward and leftward direction in FIG. 2A) of the dilation portion 120; the distal tapered portion 122a which is formed on a distal side of the cylindrical portion 121, and the outer diameter of which decreases gradually toward the distal side; and the proximal tapered portion 122b which is formed on a proximal side of the cylindrical portion 121, and the outer diameter of which decreases gradually toward the proximal side.

A proximal portion of the dilation portion 120 is fixed to a distal portion of the outer tube 111. A distal portion of the dilation portion 120 is fixed to the distal portion of the inner tube 112. Accordingly, a lumen of the dilation portion 120 communicates to the dilation lumen 111a.

The dilation portion 120 is formed of a material having flexibility to some extent. The material is not limited to a specific material. The following materials may be used as the material: polyethylene, polypropylene, polybutene, an ethylene-propylene copolymer, an ethylene-vinyl acetate copolymer, an ionomer, polyolefin which is a mixture of two or more thereof, or thermoplastic resins such as a soft polyvinylchloride resin, polyamide, a polyamide elastomer, polyester, a polyester elastomer, polyurethane, and fluororesin.

In embodiments, an exterior surface of the dilation portion 120 is coated with a bronchodilator which is a medicine capable of widening the stenosed site N. The exterior surface of the dilation portion 120 may not be coated with a bronchodilator, but multiple protruding portions 131 of the collection portion 130 (to be described later) may be impregnated with the bronchodilator. Not only the exterior surface of the dilation portion 120 may be coated with a bronchodilator, but also the multiple protruding portions 131 of the collection portion may be impregnated with the bronchodilator. The medical device 1 may not include a bronchodilator.

The collection portion 130 has the function of collecting the secretion S such as phlegm which has viscosity and stagnates in the vicinity of the stenosed site N. The collection portion 130 is attached to the inner tube 112 on the distal side of the dilation portion 120.

In embodiments, the collection portion 130 includes the multiple protruding portions 131 which protrude from the exterior surface of the inner tube 112 toward the outside of the inner tube 112. If the multiple protruding portions 131 are brought into contact with the secretion S, the secretion S enters between adjacent protruding portions 131, and the multiple protruding portions 131 are capable of suitably collecting the secretion S by entrapping the secretion S. Particularly, in an example, the secretion S is phlegm having a high viscosity, and if at least a portion of the secretion S which is one lump enters between the protruding portion 131, the protruding portions 131 are capable of efficiently collecting the secretion S by entrapping the entirety of the secretion S which is one lump. The size, length and shape of the protruding portion 131, the number of protruding portions 131, and the like are not specifically limited to those illustrated. FIGS. 2A and 2B illustrates a mode in which the protruding portions 131 extend substantially outward in a radial direction of the inner tube 112; however, an extending direction of the protruding portions 131 is not specifically limited to a direction in which the protruding portions 131 protrude from the exterior surface of the inner tube 112 toward the outside of the inner tube 112. For example, among the multiple protruding portions 131, there maybe the protruding portions 131 extending toward the proximal side, and there may be the protruding portions 131 extending toward the distal side.

The protruding portions 131 are formed of a material having flexibility such that the protruding portions 131 can be easily accommodated in the sheath 210 of the protective catheter 20 and are capable of following the shape of a biological lumen. The material is not limited to a specific material, and a microfiber formed of nylon, polyethylene, or the like may be used as the material.

As illustrated in FIG. 2B, the first hand operation portion 140 includes an outer tube hub 141 including the injection port 141a that serves as a port for the inflow and discharge of a dilation fluid, and an inner tube hub 142 including the proximal opening portion 142a that serves as a port for drawing the guide wire W.

The outer tube hub 141 is a tube shaped body with an open distal end and an open proximal end. The outer tube hub 141 is firmly fixed to a proximal portion of the outer tube 111. A firm fixation method is not limited to a specific method, and examples of the firm fixation method include, fixation using adhesion via an adhesive, heat-welding, and fixation via a fastener (not illustrated).

The inner tube hub 142 is a tube shaped body with an open distal end and an open proximal end. The inner tube hub 142 is disposed closer to the proximal side than the outer tube hub 141, and is firmly fixed to the outer tube hub 141. The inner tube hub 142 is firmly fixed to a proximal portion of the inner tube hub 112. A firm fixation method is not limited to a specific method, and examples of the firm fixation method may include adhesion via an adhesive, heat-welding, or fixation via a fastener (not illustrated).

Examples of the material of the first hand operation portion 140 include thermoplastic resins such as polycarbonate, polyamide, polysulfone, polyarylate, and a methacrylate-butylene-styrene copolymer.

Hereinafter, the protective catheter 20 will be described. As illustrated in FIG. 1, the protective catheter 20 includes the sheath 210 through which the dilation portion 120 and the collection portion 130 of the balloon catheter 10 can be inserted, and a second hand operation portion 220 that is firmly fixed to a proximal portion of the sheath 210.

The sheath 210 is a tube shaped body with an open distal end and an open proximal end. A lumen of the sheath 210 is disposed such that the dilation portion 120 and the collection portion 130 can be moved forward and rearward in the lumen in the axial direction.

Figure 5A:
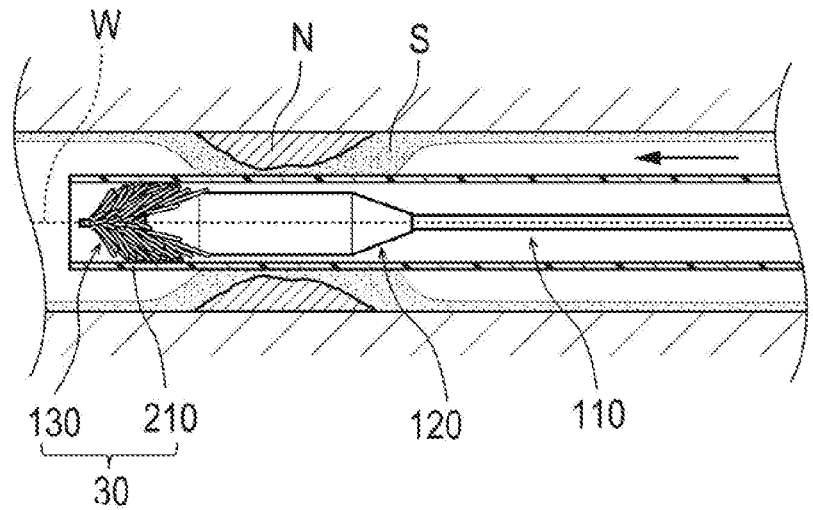
FIGS. 5A to 5C are schematic views illustrating the treatment method.

It is possible to prevent the collection portion 130 from coming into contact with the secretion S by covering the collection portion 130 with the sheath 210 until the collection 130 is disposed in the stenosed site N (refer to FIG. 5A). It is possible to discharge the secretion S from a living body by accommodating the secretion S, which has been collected by the collection portion 130, in the sheath 210 after the secretion S has been collected by the collection portion 130, and by extracting the sheath 210 from the living body (refer to FIG. 6C). The sheath 210 serves as not only a protective portion protecting the collection portion by detachably covering the collection portion, but also a discharge portion that accommodates and discharges the secretion S, which is collected by the collection portion 130, from a living body.

The sheath 210 is formed of a material having flexibility to some extent. The material is not limited to a specific material. The following materials may be used as the material: polyethylene, polypropylene, polybutene, an ethylene-propylene copolymer, an ethylene-vinyl acetate copolymer, an ionomer, polyolefin which is a mixture of two or more thereof, a polyvinylchloride resin, polyamide, a polyamide elastomer, polyester, a polyester elastomer, polyurethane, fluororesin, and the like. The sheath 210 may have a metallic mesh structure which is a reinforcement member.

The second hand operation portion 220 is a tube shaped body with an open distal end and an open proximal end. The second hand operation portion 220 is firmly fixed to the sheath 210, and thus, the lumen of the sheath 210 communicates to a lumen of the second hand operation portion 220. A firm fixation method is not limited to a specific method, and examples of the firm fixation method may include adhesion via an adhesive, heat-welding, and fixation via a fastener (not illustrated). The balloon catheter 10 is inserted into a proximal opening portion of the second hand operation portion 220.

Examples of the material of the second hand operation portion 220 include thermoplastic resins such as polycarbonate, polyamide, polysulfone, polyarylate, and a methacrylate-butylene-styrene copolymer.

Hereinafter, the treatment method of the embodiment will be described with reference to FIGS. 3 to 6.

Figure 3:
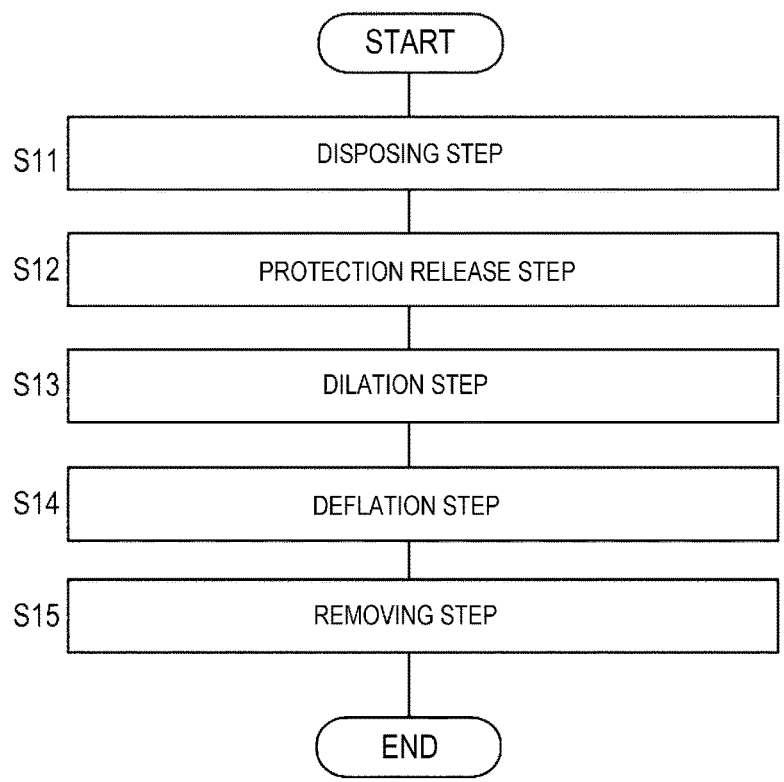
FIG. 3 is a flowchart illustrating a sequence of a treatment method.

In a brief description of the treatment method with reference to FIG. 3, the treatment method includes a disposition step (S11); a protection release step (S12); a dilation step (S13); a deflation step (S14); and a removal step (S15). Hereinafter, the steps will be described.

Figure 4:
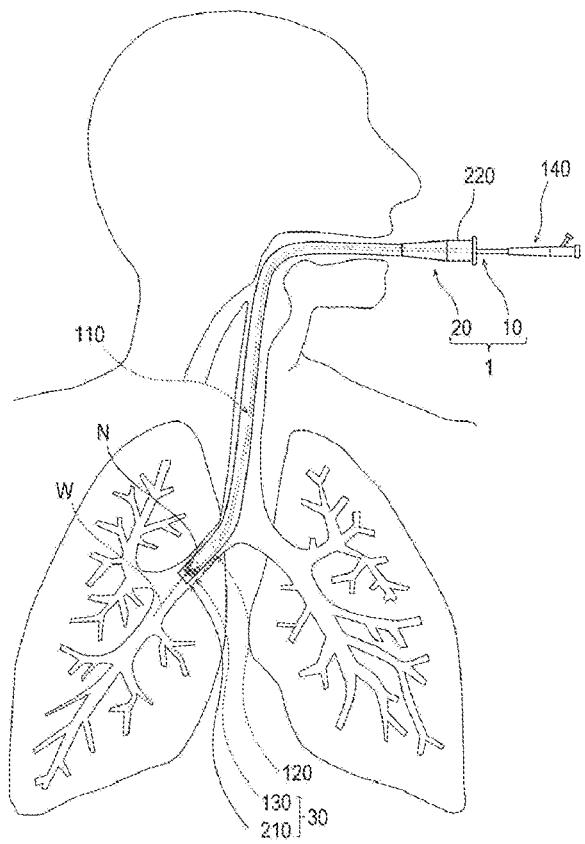
FIG. 4 is a view illustrating a mode in which the medical device is introduced into a living body.

As illustrated in FIGS. 4 and 5A, in the disposition step (S11), in a state where the dilation portion 120 and the collection portion 130 are covered with the sheath 210, the guide wire W, which has been inserted through the stenosed site N in advance, is controlled to creep such that the dilation portion 120 and the removal portion 30 (the collection portion 130 and the sheath 210) are introduced through a mouth and are disposed in the stenosed site N. At this time, the dilation portion 120 is disposed at a position where the dilation portion 120 is inserted through the stenosed site N, the collection portion 130 is disposed at a position on a distal side of the stenosed site N, and the sheath 210 is disposed at a position where the sheath 210 covers the dilation portion 120 and the collection portion 130.

Figure 5B:
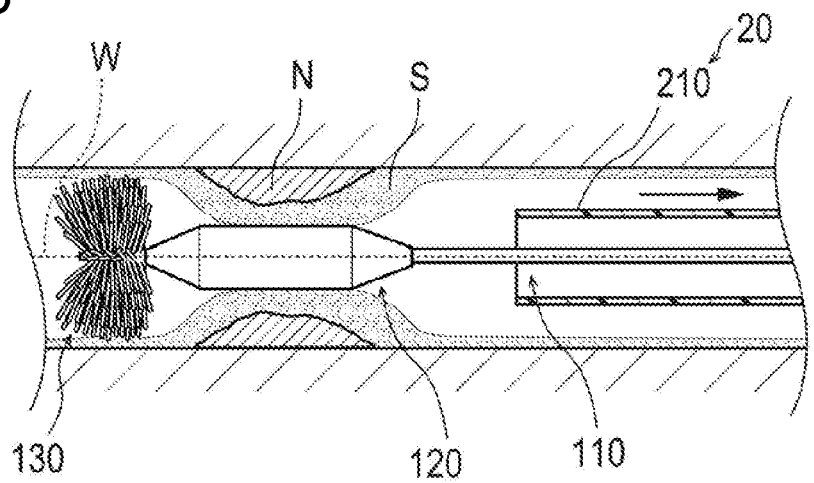

In the protection release step (S12), the second hand operation portion 220 is pulled toward the proximal side, and as illustrated in FIG. 5B, the dilation portion 120 and the collection portion 130 are exposed from the sheath 210.

Figure 5C:
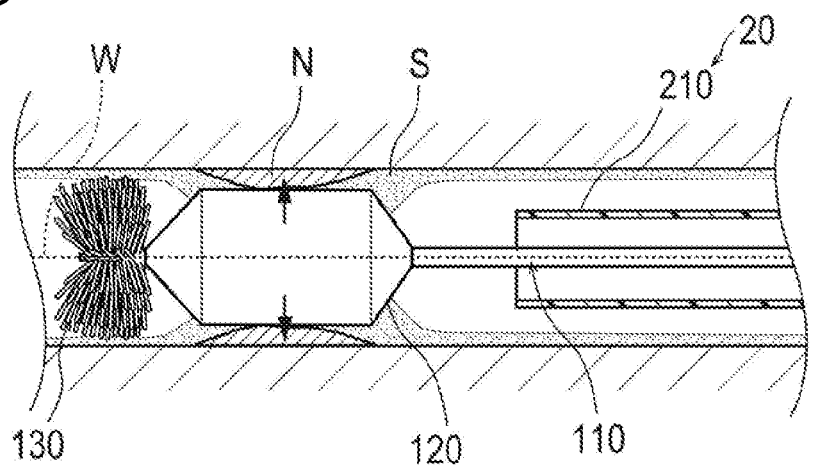

In the dilation step (S13), a fluid is injected through the injection port 141a of the balloon catheter 10, and as illustrated in FIG. 5C, the dilation portion 120 is dilated to widen the stenosed site N. If the exterior surface of the dilation portion 120 is coated with a bronchodilator, when the dilation portion 120 comes into contact with the stenosed site N, the stenosed site N is coated with the bronchodilator. As a result, it is possible to more suitably maintain a state in which the stenosed site N is widened.

Figure 6A:
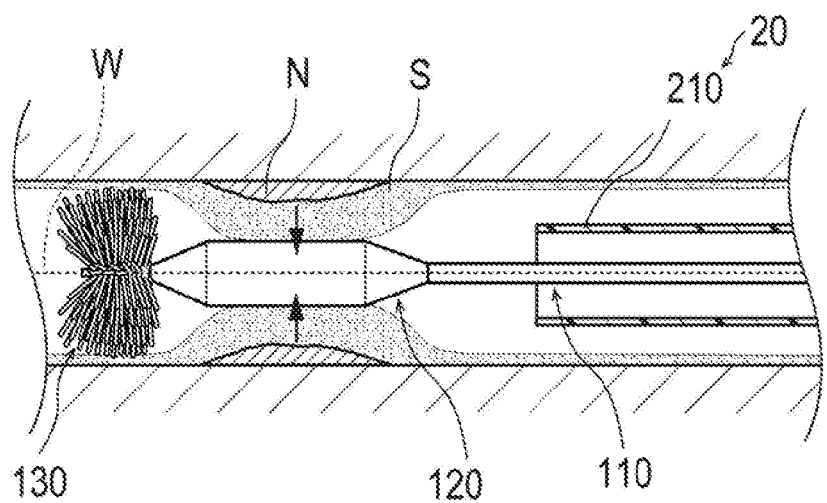
FIGS. 6A to 6C are schematic views illustrating the treatment method.

In the deflation step (S14), the fluid is discharged from the injection port 141a of the balloon catheter 10, and as illustrated in FIG. 6A, the dilation portion 120 deflates. At this time, a state in which the stenosed site N is widened is maintained.

Figure 6B:
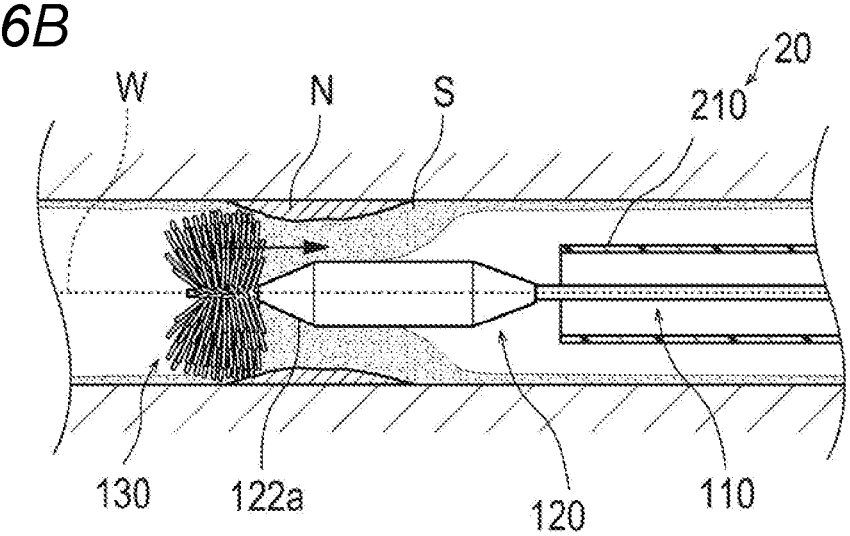
Figure 6C:
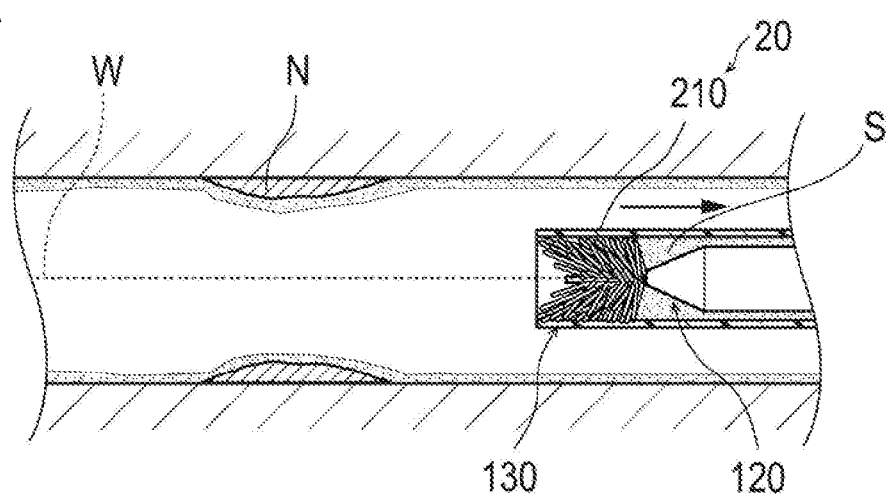

In the removal step (S15), the first hand operation portion 140 of the balloon catheter 10 is pulled toward the proximal side. Accordingly, as illustrated in FIG. 6B, the collection portion 130 is moved toward the proximal side, and as illustrated in FIG. 6C, the collection portion 130 is accommodated in the sheath 210 disposed on the proximal side. The collection portion 130 is moved toward the proximal side while the secretion S stagnating the stenosed site N is entrapped between the multiple protruding portions 131, and the secretion S is held in a recession between the distal tapered portion 122a of the dilation portion 120 and the collection portion 130. The secretion S collected by the collection portion 130 is accommodated in the sheath 210. As such, the collection portion 130 is capable of collecting a larger amount of the secretion S not only by entrapping the secretion S between the multiple protruding portions 131 but also holding the secretion S in the recession between the distal tapered portion 122a and the collection portion 130. If the collection portion 130 is impregnated with a bronchodilator, when the collection portion 130 comes into contact with the stenosed site N, the stenosed site N is coated with the bronchodilator. As a result, it is possible to more suitably maintain a state in which the stenosed site N is widened.

In the removal step (S15), as illustrated in FIG. 6C, both the first hand operation portion 140 and the second hand operation portion 220 are pulled toward the proximal side, and the medical device 1 is extracted from a living body. Accordingly, the collected secretion S is removed from the living body.

As described above, the treatment method described above includes the disposition step (S11) of disposing the dilation portion 120 that can be dilated and deflated, and the removal portion 30, which is capable of removing the secretion S secreted from a biological lumen from a living body, in the stenosed site N occurring in the biological lumen; the dilation step (S13) of widening the stenosed site N by dilating the dilation portion 120 in the stenosed site N after the disposition step (S11); and the removal step (S15) of removing the secretion S from the living body by the removal portion 30 after the disposition step (S11). For this reason, it is possible to suitably improve the obstruction of the biological lumen caused by stenosis of the biological lumen and the stagnation of the secretion S.

In the removal step (S15), the secretion S is removed from the living body with an operation of extracting the removal portion 30 from the living body. Since an addition operation such as aspiration to remove the secretion S from the living body is not required, it is possible to relatively efficiently remove the secretion S from the living body.

The removal portion 30 includes the collection portion 130 that collects the secretion S. In the disposition step (S11), the collection portion 130 is disposed in the stenosed site N in a state where the collection portion 130 is covered with the sheath 210. The treatment method further includes the protection release step (S12) of exposing the collection portion 130 from the sheath 210 before the removal step (S15). For this reason, until the collection portion 130 is disposed in a desired site (the stenosed site N), it is possible to suitably prevent the collection portion 130 from coming into contact with the secretion S, and to reliably collect the secretion S from the desired site.

In the dilation step (S13), the stenosed site N is coated with a medicine capable of widening the stenosed site N with a dilation operation in which the dilation portion 120 is dilated, and/or in the removal step (S15), the stenosed site N is coated with the medicine capable of widening the stenosed site N with a removal operation in which the removal operation 30 removes the secretion S. For this reason, it is possible to more suitably maintain a state in which the stenosed site N is widened.

The treatment method is applied to a bronchus. For this reason, it is possible to suitably improve the obstruction of the bronchus caused by stenosis of the bronchus and the stagnation of the secretion S. Accordingly, it is possible to ensure a substantial lumen of the bronchus through which air flows, and it is possible for a patient to breath more normally.

The medical device 1 includes the long shaft 110 having flexibility; the dilation portion 120 that is disposed in the distal portion of the shaft 110 and can be dilated and deflated; and the removal portion 30 that is capable of removing the secretion S secreted from a biological lumen from a living body. For this reason, it is possible to suitably improve the obstruction of the biological lumen caused by stenosis of the biological lumen and the stagnation of the secretion S.

The removal portion includes the collection portion 130 capable of collecting the secretion S. The medical device 1 further includes the sheath 210 that detachably covers the collection portion 130. For this reason, until the collection portion 130 is disposed in a desired site (the stenosed site N), it is possible to suitably prevent the collection portion 130 from coming into contact with the secretion S, and to reliably collect the secretion S from the desired site.

The collection portion 130 includes the multiple protruding portions 131 which protrude toward the outside of the inner tube 112. Since the secretion S enters between adjacent protruding portions 131, it is possible to suitably collect the secretion S by entrapping the secretion S.

The dilation portion 120 and/or the removal portion 30 include a medicine capable of widening the stenosed site N. For this reason, the stenosed site N is coated with the medicine with the dilation of the dilation portion 120 and/or the removal of the secretion S by the removal portion 30, and thus, it is possible to more suitably maintain a state in which the stenosed site N is widened.

Figure 7A:
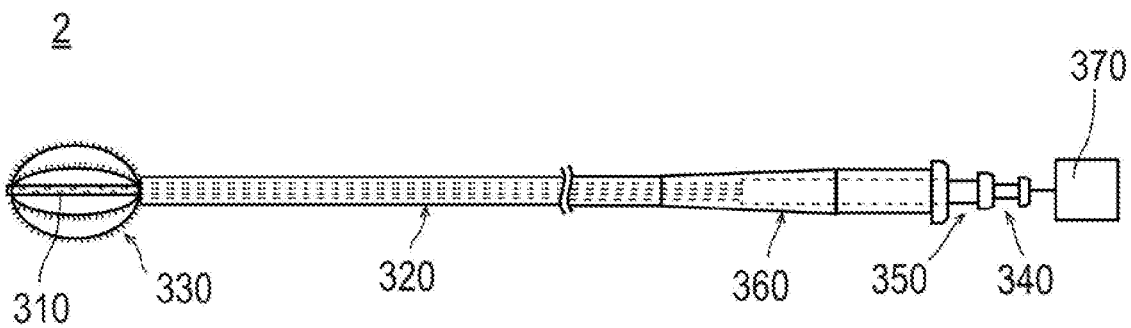
FIG. 7A is a view illustrating the entire configuration of a medical device.
Figure 7B:
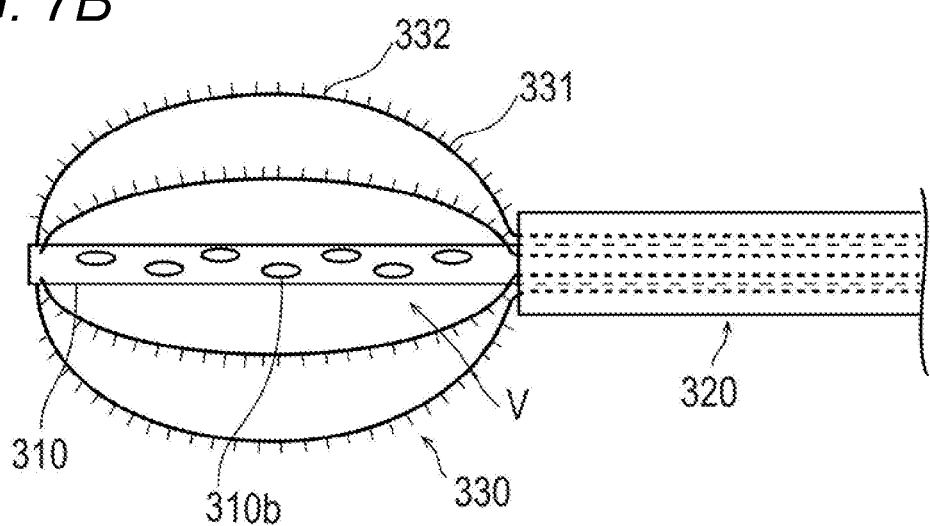
FIG. 7B is an enlarged top view illustrating a distal portion of the medical device.
Figure 7C:
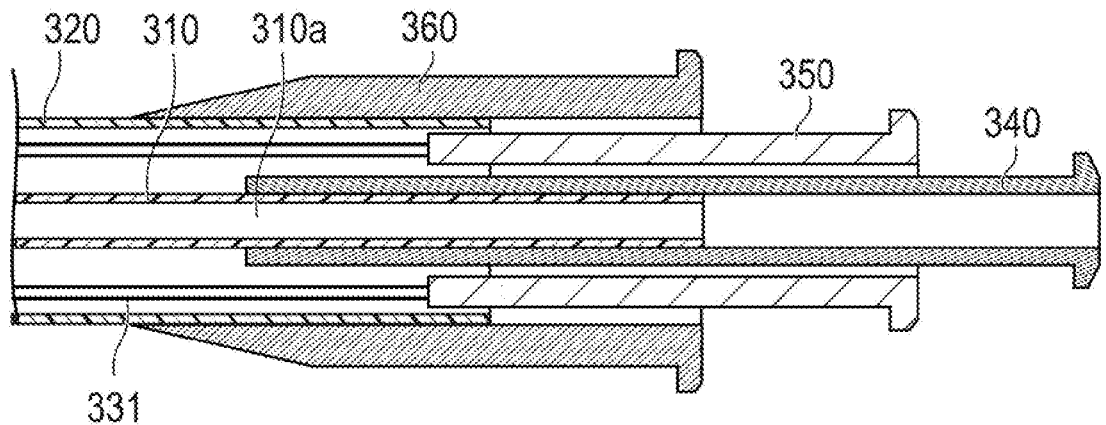
FIG. 7C is an enlarged sectional view illustrating a proximal portion of the medical device.

Hereinafter, a second example of a treatment method and a medical device 2 will be described with reference to FIGS. 7A to 10C. FIGS. 7A through 7C show views provided to describe each part of the medical device 2. FIGS. 8 to 10C are views provided to describe the treatment method.

Similar to the first example described above, the medical device 2 is a medical device used to ensure a substantial lumen of a bronchus through which air is capable of flowing by widening the stenosed site N formed in the bronchus, and removing the secretion S such as phlegm, that is secreted from the bronchus. The medical device 2 is different from the first medical device 1 in that a deformation member 330 (to be described later) serves as both a dilation portion widening the stenosed site N formed in the bronchus and a collection portion collecting the secretion S. Hereinafter, the medical device 2 will be described in detail.

The medical device 2 includes a long shaft 310 having flexibility; a sheath (equivalent to a "protective portion") 320 that covers the shaft 310; the deformation member (equivalent to a "dilation portion" and a "collection portion") 330 that is provided between the shaft 310 and the sheath 320; a discharge port 340 that is attached to a proximal side of the shaft 310; a first hand operation portion 350 that is attached to a proximal side of the deformation member 330; a second hand operation portion 360 that is attached to a proximal side of the sheath 320; and a discharge portion 370 that is connected to the discharge port 340, and aspirates and discharges the secretion S from a living body. In embodiments, a removal portion which removes the secretion S from the living body includes the deformation member 330 and the discharge portion 370.

As illustrated in FIGS. 7B and 7C, the shaft 310 is a tube shaped body with an open distal end and an open proximal end. The shaft 310 includes a secretion lumen 310a through which the secretion S flows. A distal portion of the shaft 310 is provided with multiple holes 310b which pass through the shaft 310 in a thickness direction.

An extending direction of the shaft 310 is referred to as an axial direction, a side of the shaft 310 in the axial direction which is inserted into an organ is referred to as a distal side, and a hand-side of the shaft 310 in the axial direction in which the discharge port 340 is provided is referred to as a proximal side. A distal portion indicates a predetermined range including a distal end (distalmost end) and the vicinity of the distal end. A proximal portion indicates a predetermined range including a proximal end (proximalmost end) and the vicinity of the proximal end.

The sheath 320 is a tube shaped body with an open distal end and an open proximal end. The shaft 310 and the deformation member 330 are disposed in a lumen of the sheath 320 in such a way as to be capable of being moved forward and rearward in the axial direction, and being rotated in a circumferential direction. The proximal portion of the sheath 320 is firmly fixed to the second hand operation portion 360. It is possible to adjust the exposed lengths of the distal sides of the shaft 310 and the deformation member 330 with respect to the sheath 320 by moving the second hand operation portion 360 forward and rearward in the axial direction.

The shaft 310 and the sheath 320 are formed of a material having flexibility to some extent. The material is not limited to a specific material. The following materials may be used as the material: polyethylene, polypropylene, polybutene, an ethylene-propylene copolymer, an ethylene-vinyl acetate copolymer, an ionomer, polyolefin which is a mixture of two or more thereof, a polyvinylchloride resin, polyamide, a polyamide elastomer, polyester, a polyester elastomer, polyurethane, fluororesin, and the like. The sheath 320 may have a metallic mesh structure which is a reinforcement member.

The deformation member 330 includes multiple wires 331 which extend from a distal side of the shaft 310 toward the proximal side, and a large number of protruding portions 332 which protrude from the exterior of each of the wires 331 toward the outside of the wire 331.

Distal portions of the wires 331 are fixed to the distal portion of the shaft 310. Proximal portions of the wires 331 are fixed to the first hand operation portion 350. If the first hand operation portion 350 is pressed toward the distal side in a state where the distal sides of the shaft 310 and the wires 331 are exposed from the sheath 320, as illustrated in FIG. 9C, the distal sides of the wires 331 are deformed into a shape in which the distal sides of the wires 331 are convexly curved toward the outside of the shaft 310 (that is, a distal portion of the deformation member 330 dilates). If the first hand operation portion 350 is pulled toward the proximal side in this state, as illustrated in FIG. 10B, the distal portions of the wires 331 are deformed to approach the shaft 310 (that is, the distal portion of the deformation member 330 dilates). As such, the distal portion of the deformation member 330 serves as a dilatable and deflatable dilation portion.

Figure 9A:
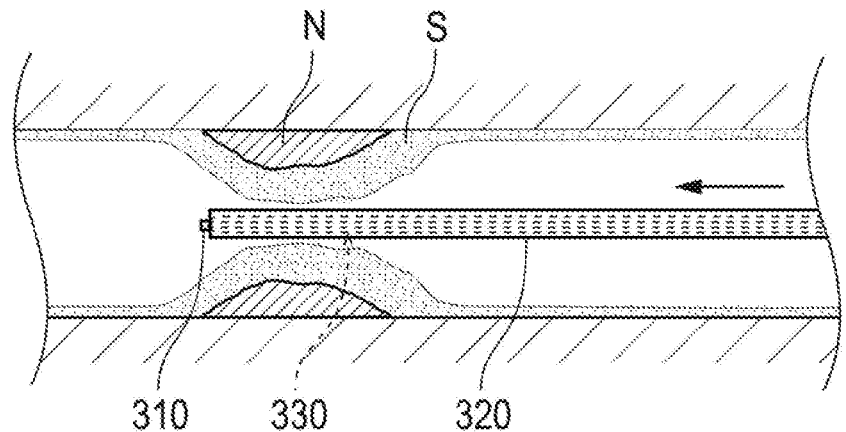
FIGS. 9A to 9C are schematic views illustrating the treatment method.
Figure 9B:
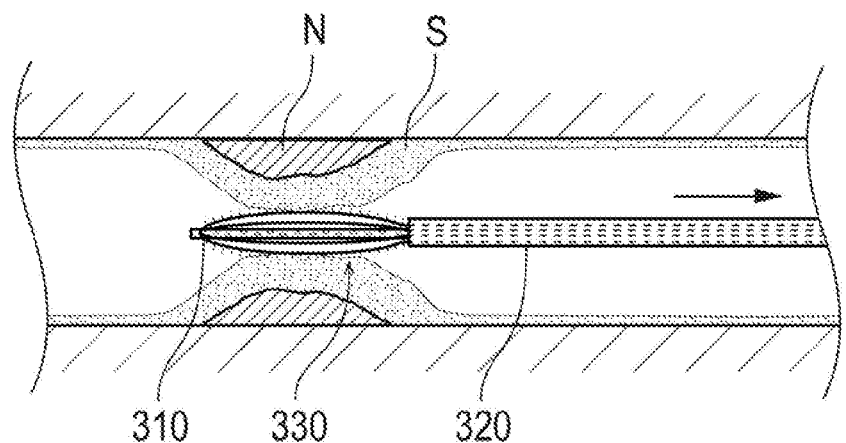
Figure 9C:
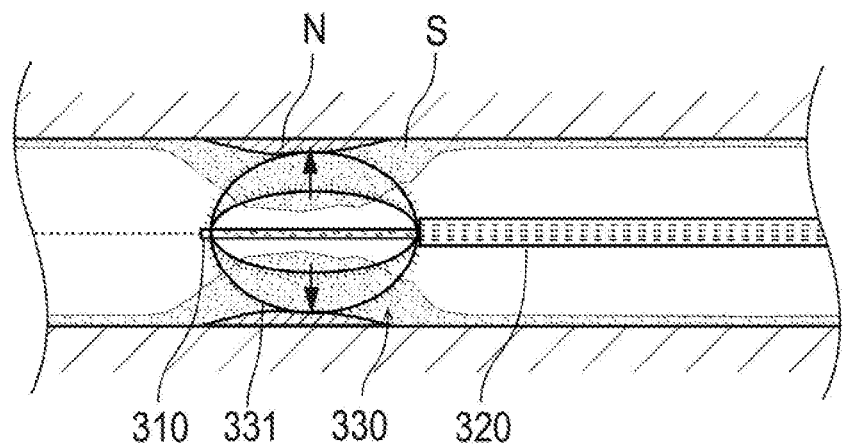
Figure 10A:
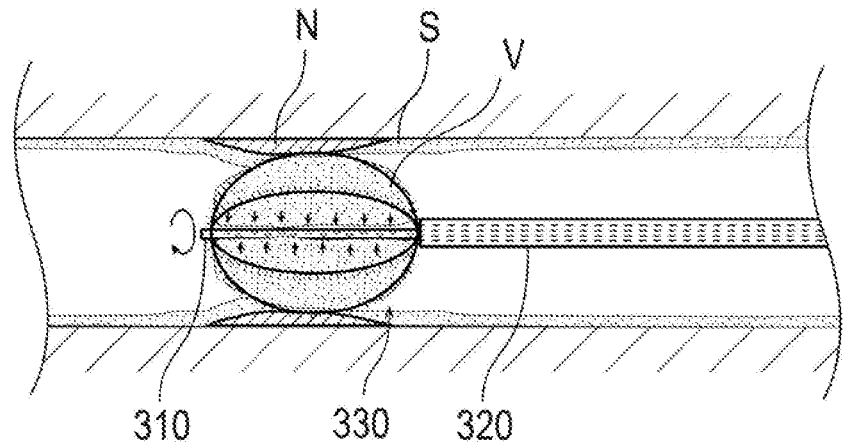
FIGS. 10A to 10C are schematic views illustrating the treatment method.
Figure 10B:
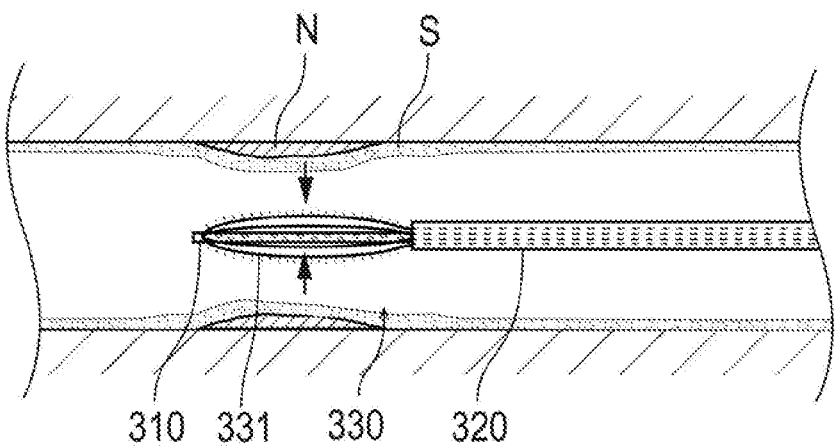
Figure 10C:
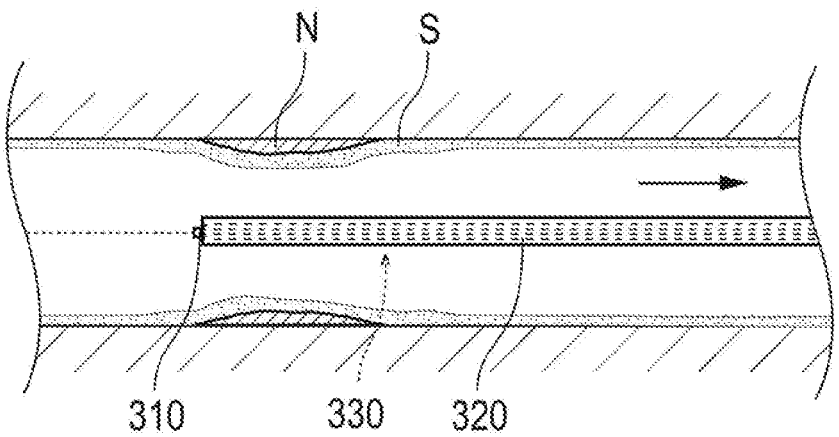

If the wires 331 are brought into contact with the secretion S in a state where the distal portions of the wires 331 are convexly curved toward the outside of the shaft 310, the secretion S enters a space V surrounded by curved portions of the multiple wires 331 (refer to FIGS. 9C and 10A). It is possible to suitably entrap the secretion S by accommodating the secretion S in the space V.

The wires 331 are formed of a material having hardness to the extent of being able to widen the stenosed site N, and having flexibility to some extent. Stainless steel (SUS304), β titanium steel, a Co—Cr alloy, a nickel-titanium alloy, or the like may be used as the material.

The multiple protruding portions 332 are formed into a pilus-like shape on an exterior surface of each of the wires 331. If the multiple protruding portions 332 are brought into contact with the secretion S, the secretion S enters between adjacent protruding portions 332, and thus, it is possible to suitably entrapping the secretion S. Particularly, the secretion S is phlegm having a high viscosity, and if at least a portion of the secretion S which is one lump enters between the protruding portion 332, the protruding portions 332 are capable of efficiently collecting the secretion S by entrapping the entirety of the secretion S which is one lump. The size, length and shape of the protruding portion 332, the number of protruding portions 332, and the like are not specifically limited to those illustrated.

The multiple protruding portions 332 are preferably formed of a material having flexibility, and a microfiber formed of nylon, polyester, or the like may be used as the material.

As such, the deformation member 330 also serves as a collection portion that collects the secretion S by entrapping the secretion S by the curved wires 331 and the multiple protruding portions 332.

In embodiments, the multiple protruding portions 332 are impregnated with a bronchodilator. The medical device 2 may not include a bronchodilator.

As illustrated in FIG. 7C, each of the discharge port 340, the first hand operation portion 350, and the second hand operation portion 360 is a tube shape body with an open distal end and an open proximal end.

The discharge port 340 is firmly fixed to a proximal portion of the shaft 310, and thus, the secretion lumen 310a of the shaft 310 communicates to a lumen of the discharge port 340. A firm fixation method is not limited to a specific method, and examples of the firm fixation method may include adhesion via an adhesive, heat-welding, and fixation via a fastener (not illustrated).

A distal portion of the first hand operation portion 350 is attached to a proximal portion of the deformation member 330. The distal sides of the shaft 310 and the discharge port 340 are disposed in a lumen of the first hand operation portion 350 in such a way as to be capable of being moved forward and rearward. Accordingly, it is possible to adjust the exposed length of the wires 331 with respect to the sheath 320 while maintaining the position of distal ends of the wires 331 with respect to the shaft 310 at a predetermined position (that is, it is possible to adjust the dilation and deflation of the distal side of the deformation member 330).

A distal portion of the second hand operation portion 360 is attached to the proximal portion of the sheath 320. The shaft 310, the discharge port 340, the deformation member 330, and the first hand operation portion 350 are disposed in a lumen of the second hand operation portion 360 in such a way as to be capable of being moved forward and rearward and being rotated in the circumferential direction.

Examples of the materials of the discharge port 340, the first hand operation portion 350, and the second hand operation portion 360 include thermoplastic resins such as polycarbonate, polyamide, polysulfone, polyarylate, and a methacrylate-butylene-styrene copolymer.

Insofar as the discharge portion 370 is capable of aspirating the secretion S inside the shaft 310 and discharging the secretion S from a living body, the discharge portion 370 is not limited to a specific type. For example, the discharge portion 370 may be an aspiration pump. If the discharge portion 370 is connected to the discharge port 340, and performs aspiration, the secretion S is taken into the shaft 310 via an opening portion and the multiple holes 310b on the distal side of the shaft 310, and the secretion S is discharged from the living body via the secretion lumen 310a.

Hereinafter, the treatment method associated with medical device 2 will now be described with reference to FIGS. 8 to 10C.

Figure 8:
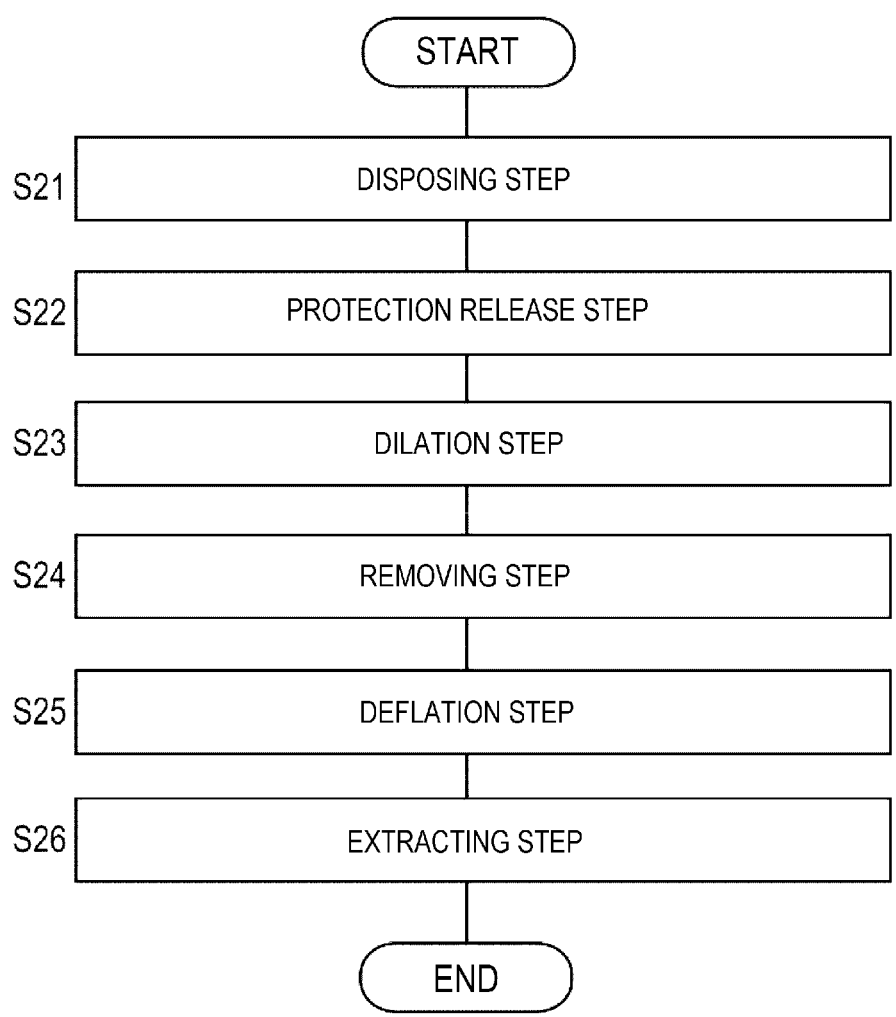
FIG. 8 is a flowchart illustrating a sequence of a treatment method of the second embodiment.

In a brief description of the treatment method with reference to FIG. 8, the treatment method includes a disposition step (S21); a protection release step (S22); a dilation step (S23); a removal step (S24); a deflation step (S25); and an extraction step (S26). Hereinafter, the steps will be sequentially described.

As illustrated in FIG. 9A, in the disposition step (S21), in a state where the distal sides of the shaft 310 and the deformation member 330 are covered with the sheath 320, a distal side of the medical device 2 is introduced through a mouth, and the distal portion of the deformation member 330 is disposed to be inserted through the stenosed site N.

In the protection release step (S22), the second hand operation portion 360 of the sheath 320 is pulled toward the proximal side, and as illustrated in FIG. 9B, the distal portions of the shaft 310 and the deformation member 330 are exposed from the sheath 320.

In the dilation step (S23), the first hand operation portion 350 is pressed toward the distal side, and as illustrated in FIG. 9C, the distal portion of the deformation member 330 dilates to widen the stenosed site N. If the multiple protruding portions 332 are impregnated with a bronchodilator, when the protruding portions 332 are brought into contact with the stenosed site N, the stenosed site N is coated with the bronchodilator. As a result, it is possible to more suitably maintain a state in which the stenosed site N is dilated.

In the removal step (S24), as illustrated in FIG. 10A, the first hand operation portion 350 is rotated in the circumferential direction, and the discharge portion 370 is operated to aspirate the secretion S. With the rotation of the first hand operation portion 350, it is possible to accommodate the secretion S in the space V surrounded by the multiple curved wires 331, and between the multiple protruding portion 332, and to suitably collect the secretion S. The collected secretion S is removed from the living body by aspiration performed by the discharge portion 370.

In the deflation step (S25), the first hand operation portion 350 is pulled toward the proximal side, and as illustrated in FIG. 10B, the distal portion of the deformation member 330 deflates.

In the extraction step (S26), the discharge port 340 and the first hand operation portion 350 are pulled toward the proximal side, and the distal portions of the shaft 310 and the deformation member 330 are accommodated in the sheath 320. After accommodation, the discharge port 340, the first hand operation portion 350, and the second hand operation portion 360 are pulled toward the proximal side, and the medical device 2 is extracted from the living body.

As described above, in the medical device 2, the deformation member 330 has the space V capable of accommodating the secretion S. For this reason, it is possible to collect a larger amount of the secretion S.

The treatment method and the medical device have been described with reference to multiple embodiments; however, the embodiments are not limited to only the aforementioned configurations, and the embodiments can be suitably changed based on the claims.

Insofar as the medical device of the embodiments herein includes a long shaft having flexibility, a dilation portion that is disposed in a distal portion of the shaft and can be dilated and deflated, and a removal portion that is capable of removing a secretion, which is secreted from a biological lumen, from a living body, the medical device is not limited to a specific configuration. For example, a medical device may include a self-expansion stent (equivalent to a "dilation portion"), and a self-expansion stent delivery catheter including a removal portion that removes a secretion from a living body. For example, a medical device may include a stent (equivalent to a "dilation portion"), and a stent delivery balloon catheter including a removal portion that is capable of removing a secretion from a living body. In this case, the stent may be a bare-metal stent (BMS), a drug eluting stent (DES), or a bioresorbable stent (BRS).

A site to which the treatment method and the medical device of the embodiments herein are applied is not limited to a bronchus. The treatment method and the medical device can be applied to a stenosed site occurring in sites other than a trachea, a blood vessel, a biliary duct, an esophagus, a urethra, or other biological lumens.

In embodiments, the collection portion 130 is disposed on the distal side of the dilation portion 120. Alternatively, the collection portion 130 may be disposed on a proximal side of the dilation portion 120 (in the distal portion of the outer tube 111). In this case, a treatment method is performed as follows. After the collection portion 130 and the dilation portion 120 covered with the sheath 210 are disposed on the distal side of the stenosed site N (disposition step), the secondhand operation portion 220 is pulled toward the proximal side, and the dilation portion 120 and the collection portion 130 are exposed from the sheath 210 (protection release step). Subsequently, the first hand operation portion 140 is pulled toward the proximal side, and thus, the dilation portion 120 is inserted through the stenosed site N, and the secretion S is entrapped and collected while the collection portion 130 is moved from the distal side of the stenosed site N toward a proximal side thereof (collection step). Subsequently, after the stenosed site N is widened by dilating the dilation portion 120 in the stenosed site N (dilation step), the dilation portion 120 is deflated (deflation step). Subsequently, the first hand operation portion 140 is pulled toward the proximal side, and the dilation portion 120 and the collection portion 130 are accommodated in the sheath 210. As a result, the collected secretion S is accommodated in the sheath 210, and then the medical device is extracted from a living body (extraction step). In this case, a removal step of removing the secretion S from the living body includes the collection step and the extraction step. The removal step is executed before and after the dilation step. If the removal step and the dilation step are executed after the disposition step, a sequence in which the removal step and the dilation step are executed is not limited to a specific sequence. As described above, the removal step may be executed before and after the dilation step, or the removal step may be executed before the dilation step.

Figure 11:
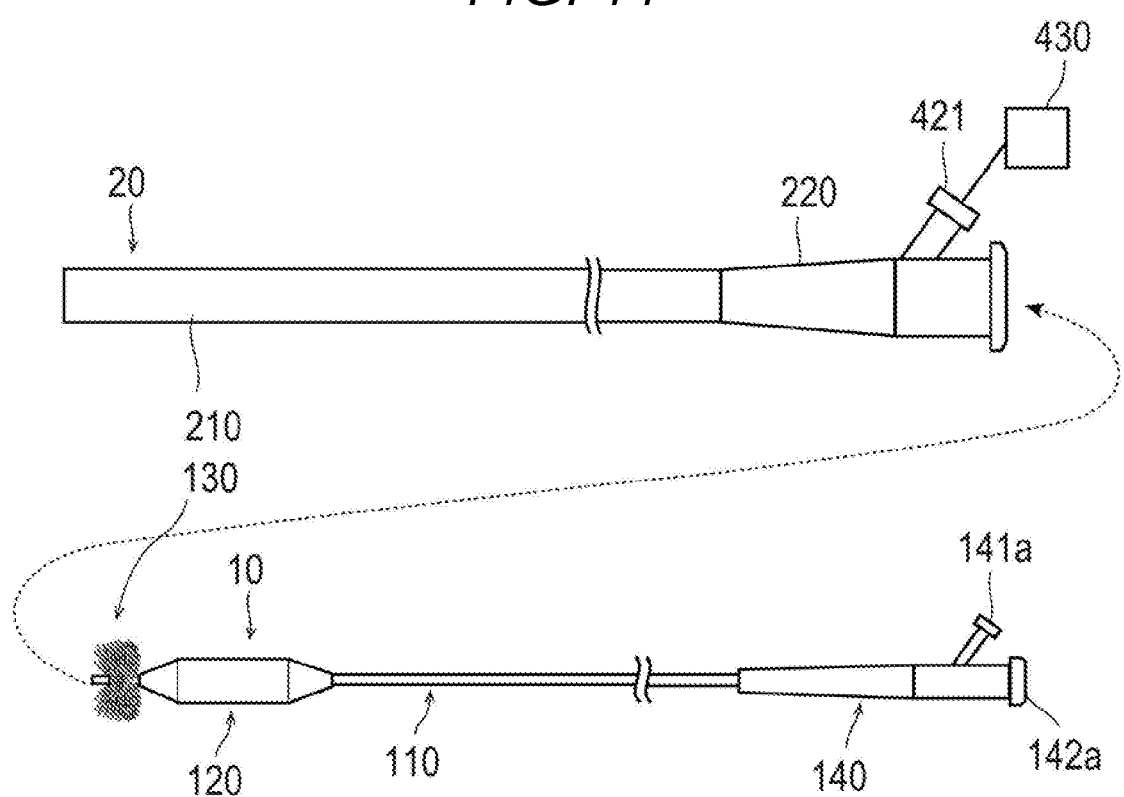
FIG. 11 is a schematic view illustrating the entire configuration of a medical device of a modification example.

In embodiments, the secretion S is removed from a living body with an operation of extracting the removal portion 30 from the living body. Alternatively, as illustrated in FIG. 11, a discharge port 421 through which the secretion S is discharged may be provided in the secondhand operation portion 220 of the protective catheter 20, and the secretion S accommodated in the sheath 210 may be discharged from a living body by a discharge portion 430 such as an aspiration pump which is connected to the discharge port 421. In this case, the removal portion which removes the secretion S from the living body includes the collection portion 130 and the discharge portion 430.

In embodiments, the collection portion is configured of the multiple protruding portions formed of a microfiber. Insofar as the collection portion is configured to be capable of collecting a secretion, the collection portion is not limited to a specific configuration. For example, the collection portion may be a spatula-shaped member formed of a material such as sponge or silicon having flexibility.

In embodiments, the balloon catheter may be provided with a mechanism capable of rotating in a circumferential direction, and in the removal step, a secretion may be more suitably collected by rotating the balloon catheter (collection portion) in the circumferential direction.

In embodiments, the medical device 2 includes the discharge portion 370. Alternatively, the medical device 2 may not include the discharge portion 370, and the removal portion which removes the secretion S from a living body may include the deformation member 330 that collects the secretion S, and the sheath 320 that is capable of accommodating the secretion S collected by the deformation member 330, and discharging the secretion S from the living body with an extraction operation. In this case, the holes 310b may not be provided in the shaft, and the medical device may not include the discharge portion 340.

DESCRIPTION OF REFERENCE NUMERALS AND SIGNS 1, 2 MEDICAL DEVICE
10 BALLOON CATHETER
20 PROTECTIVE CATHETER
30 REMOVAL PORTION
110 SHAFT
120 DILATION PORTION
130 COLLECTION PORTION
131 PROTRUDING PORTION
210 SHEATH (PROTECTIVE PORTION)
310 SHAFT
320 SHEATH (PROTECTIVE PORTION)
330 DEFORMATION MEMBER (DILATION PORTION AND COLLECTION PORTION)
331 WIRE
332 PROTRUDING PORTION
370 DISCHARGE PORTION
N STENOSED SITE
S SECRETION
V SPACE
W GUIDE WIRE

What is claimed is:

1. A treatment method comprising:
introducing a sheath of a catheter into a biological lumen of a living body and in a direction toward a stenosed site in the biological lumen;
advancing a distal tip of the sheath from a proximal side of the stenosed site in the biological lumen through the stenosed site to a distal side of the stenosed site in the biological lumen;
positioning, while a portion of the sheath is disposed in the stenosed site, a shaft disposed inside a lumen of the sheath at a postion of the stenosed site;
withdrawing the sheath from the stenosed site while maintaining the shaft in the position of the stenosed site, wherein withdrawing the sheath exposes a portion of the shaft form the lumen of the sheath such that i) a dilation balloon portion of the shaft is arranged in the stenosed site, ii) a removal portion of the shaft comprising a plurality of protruding portuions is disposed on the distal side of the stenosed site, and iii) the sheath is disposed on the proximal side of the stenosed site, and wherein the plurality of protruding portions are capable of removing a secretion secreted from the biological lumen in the stenosed site;
widening the stenosed site by dilating the dilation balloon portion of the shaft while arranged in the stenosed site;
deflating the dilation balloon portion of the shaft while arranged in the stenosed site; and
removing the secretion from the biological lumen by moving the plurality of protruding portions from the distal side of the stenosed site into contact with the secretion in the stenosed site entrapping the secretion in the plurality of protruding portions and then moving the plurality of protruding portions and the secretion entrapped therein from the stenosed site to the proximal side of the stenosed site.

2. The treatment method according to claim 1, wherein in the removal step, the secretion is removed from the living body with an operation of extracting the removal portion from the living body through the lumen of the sheath.

3. The treatment method according to claim 2, wherein the secretion is collected in between the plurality of protruding portions as the plurality of protruding portions are moved from the distal side of the stenosed site to the proximal side of the stenosed site.

4. The treatment method according to claim 3, wherein an exterior surface of the dilation balloon portion of the shaft is coated with a medicine capable of widening the stenosed site upon dilation of the dilation balloon portion of the shaft moving the exterior surface of the dilation balloon portion into contact with the stenosed site.

5. The treatment method according to claim 4, wherein the biological lumen is a bronchus.

6. The treatment method according to claim 1, wherein the secretion is collected in between the plurality of protruding portions as the plurality of protruding portions are moved from the distal side of the stenosed site to the proximal side of the stenosed site.

7. The treatment method according claim 1, wherein an exterior surface of the dilation balloon portion of the shaft is coated with a medicine capable of widening the stenosed site upon dilation of the dilation balloon portion of the shaft moving the exterior surface of the dilation balloon portion into contact with the stenosed site.

8. The treatment method according claim 2, wherein an exterior surface of the dilation balloon portion of the shaft is coated with a medicine capable of widening the stenosed site upon dilation of the dilation balloon portion of the shaft moving the exterior surface of the dilation balloon portion into contact with the stenosed site, and wherein the plurality of protruding portions are impregnated with the medicine.

* * * * *